United States Patent [19]
Ladisch et al.

[11] Patent Number: 5,846,787
[45] Date of Patent: Dec. 8, 1998

[54] PROCESSES FOR TREATING CELLULOSIC MATERIAL

[75] Inventors: Michael R. Ladisch, West Lafayette; Karen L. Kohlman, Carmel, both of Ind.; Paul L. Westgate, Columbia, Md.; Joseph R. Weil, West Lafayette, Ind.; Yiqi Yang, Charlottesville, Va.

[73] Assignee: Purdue Research Foundation Office of Technology Transfer, West Lafayette, Ind.

[21] Appl. No.: 273,417

[22] Filed: Jul. 11, 1994

[51] Int. Cl.$^6$ ........................................ C12P 19/14
[52] U.S. Cl. .............................. 435/99; 435/105; 435/209
[58] Field of Search ........................................ 435/209, 105, 435/99, 165, 163, 252

[56] References Cited

U.S. PATENT DOCUMENTS

| | | | |
|---|---|---|---|
| 1,687,785 | 10/1928 | Perl | 127/37 |
| 4,237,226 | 12/1980 | Grethlein | 435/99 |
| 4,425,433 | 1/1984 | Neves | 435/163 |
| 4,461,648 | 7/1984 | Foody | 127/37 |
| 4,645,541 | 2/1987 | DeLong | 127/37 |

OTHER PUBLICATIONS

Kohlmann et al, 1993, Proc. ICES Meeting, SAE Tech. Paper 932251 pp. 1–8.
Mithel et al, TAPPI, 1957, vol. 40, pp. 1–4.
Ladisch et al., Proc. $9^{th}$ Int. Biotech Symp. & Exposition, ASM, 1992, pp. 510–518.
Hormeyer et al, Holzforschung, 42(2), pp. 95–98, 1988.
Weil, J.R, M.S. Thesis, May 1993 pp. 1–79, Purdue University.

*Primary Examiner*—Irene Marx
*Attorney, Agent, or Firm*—Woodard, Emhardt, Naughton, Moriarty & McNett

[57] ABSTRACT

Disclosed are processes for pretreating cellulosic materials in liquid water by heating the materials in liquid water at a temperature at or above their glass transition temperature but not substantially exceeding 220° C., while maintaining the pH of the reaction medium in a range that avoids substantial autohydrolysis of the cellulosic materials. Such pretreatments minimize chemical changes to the cellulose while leading to physical changes which substantially increase susceptibility to hydrolysis in the presence of cellulase.

23 Claims, 7 Drawing Sheets

PROCESSES FOR TREATING CELLULOSIC MATERIAL

This invention was made with Government support under Grant No. CSR90-37233-5410, awarded by the USDA and through the NASA NSCORT Center at Purdue University. The Government has certain rights in the invention.

The present invention relates generally to cellulose chemistries, and more particularly to processes for pretreating cellulosic materials to modify their physical properties, for example to increase their susceptibility to enzymatic hydrolysis by cellulase enzymes.

When cellulases are added to lignocellulosic substrates, there is a dramatic decrease in the hydrolysis rate during the first few hours of the reaction. This rapid decline in the hydrolysis rate of cellulose has been widely reported and is more pronounced for pretreated substrates than native materials (Ladisch et al., 1978; Ladisch et al., 1992). Reasons for this decline, as reported by Nidetzky and Steiner (1993), include thermal instability of the enzyme, product inhibition by glucose or cellobiose, inactivation of the adsorbed enzyme (due to diffusion into the cellulose fibrils), transformation of the more susceptible portions of the substrate to sugars leaving a less digestible form, and the general heterogeneous structure of the substrate. Cellulose is associated both chemically and physically with lignin and physically with hemicellulose in plants. Both the lignin and hemicellulose protect the cellulose from hydrolysis (Ladisch et al., 1983; Ladisch, 1989). In this regard, hemicelluloses are generally linear and branched polymers of pentoses, but may include some hexoses, uronic acids, methoxy moities and acetyl groups. Lignin is a three-dimensional polymeric matrix of aromatic structures.

Pretreatments chemically and/or physically help to overcome resistance to enzymatic hydrolysis and are used to enhance cellulase action. Physical pretreatments for plant lignocellulosics include size reduction, steam explosion, irradiation, cryomilling, and freeze explosion. Chemical pretreatments include dilute acid hydrolysis, buffered solvent pumping, alkali or alkali/$H_2O_2$ delignification, solvents, ammonia, and microbial or enzymatic methods (Marsden and Gray, 1986).

Pulping processes use water to cook wood materials in order to remove lignin and obtain pulping grade celluloses suitable for making paper (Sjostrom, 1981). Reagents added to assist pulping processes in acid sulfite pulping (140° C., pH 1–2) result in effective delignification; in a neutral solution the lignin would remain insoluble.

Water-based pretreatments should be ideal for applications which demand strict safety requirements and/or environmentally compatible conditions. Bobleter et al. (1976), first used a water approach as a pretreatment to enhance susceptibility of lignocellulosic material to enzymatic hydrolysis. High temperature steam has previously been used as a pretreatment agent in the well documented hydrothermolysis and steam explosion pretreatments. Hydrothermolysis studies such as those by Haw et al. (1985), Hormeyer et al. (1988), and Walch et al. (1992), have shown that the primary effects of hot water pretreatment are a removal/solubilization of hemicellulose which is catalyzed by small quantities of acid and solubilization of some of the lignin at high temperatures (>180° C.). Brownell and Saddler (1987), report that steam pretreatment of lignocellulosic material was at least as effective for pretreatment of aspen chips, that neither the explosion or temperatures above 190° C. were necessary. Mok and Antal (1992), found that at 230° C., amorphous cellulose was also solubilized. It has generally been accepted that crystalline cellulose is unaffected by hot liquid water pretreatment.

In steam explosion, steam penetrates the lignin, hemicellulose, and cellulose. The mixture is explosively decompressed, and the resulting expansion increases cellulose accessibility (Beltrame et al., 1992). The operating conditions promote acid formation and result in degradation of cellulose by autohydrolysis. This phenomenon is considered to be an important and necessary aspect of pretreatment (Beltrame et al., 1992, Heitz et al., 1991).

Many process schemes for biotechnological use of lignocellulosic materials ignore possible uses of lignin, other than suggesting that it be burned for energy recovery. Leisola and Fiechter (1985), point out that an efficient mechanism for lignin degradation exists in nature since no accumulation occurs, lignin either degrades to $CO_2$ and $H_2O$ or is converted to humus. Lignin is degraded by a narrower array of microbes than any other major biopolymer (Kirk and Farrell, 1987). White-rot fungi (Basidiomycotina) are of special interest because lignin is attacked simultaneously with cellulose and hemicellulose; the wood becomes pale as the pigmented lignin is removed (Hudson, 1986).

Despite much previous effort relative to cellulose pretreatments, there remains a need for effective cellulose pretreatments which are inexpensive, simple, safe and environmentally desirable to conduct. The present invention addresses this need.

SUMMARY OF THE INVENTION

Accordingly, one preferred embodiment of the invention provides a process for treatment of a cellulosic material in which temperature and pH conditions in a liquid water medium are controlled to provide dramatic improvement in the ability of cellulase to catalyze hydrolysis of the cellulosic material. In accordance with the invention, the cellulosic material is pretreated by a process including charging the material to a reactor containing liquid water to form a pretreatment medium, and heating the pretreatment medium to a temperature of about 160° C. to about 220° C. while maintaining the pH of the pretreatment medium in the range of about 5 to about 8. The cellulosic material thus pretreated is thereafter contacted with a cellulase enzyme to enzymatically hydrolyze the cellulosic material. In these processes, the optimum pH and temperature of the enzyme are preferably employed. Therefore, in preferred processes, the pretreated material can be left in situ in the pretreatment medium which can be adjusted to the appropriate conditions prior to enzyme addition.

In another aspect, the invention provides a process for enzymatically hydrolyzing a pretreated cellulosic material. The process includes enzymatically hydrolyzing a pretreated cellulosic material in the presence of a cellulase enzyme, wherein the cellulosic material is the product of a pretreatment process in which the cellulosic material is heated in a liquid water medium to a temperature of about 160° C. to about 220° C. while maintaining the pH of the liquid water medium in the range of about 5 to about 8, so as to increase the susceptibility of the cellulosic material to hydrolysis by the cellulase enzyme.

A further preferred embodiment of the invention provides a process for pretreating microcrystalline cellulose to increase its susceptibility to hydrolysis by a cellulase enzyme. This process include the steps of pretreating microcrystalline cellulose by heating the microcrystalline cellulose in a liquid water medium at a temperature of about 160° C. to about 220° C.; controlling the pH of the liquid water medium during the period that it is in said temperature range, so as to maintain the pH of the liquid water medium in the range of about 5 to about 7; and recovering therefrom a pretreated microcrystalline cellulose having an increased susceptibility to hydrolysis by a cellulase enzyme.

Still another preferred embodiment of the invention provides a process for pretreating a crude plant cellulose material containing hemicellulose and lignin to increase the susceptibility of the cellulose material to hydrolysis by a cellulase enzyme. This preferred process includes charging the plant cellulose material and water to a reactor to form a pretreatment mixture. This mixture is then heated to a temperature of at least about 160° C. but not exceeding about 220° C., the pH of the pretreatment mixture during said heading being in the range of about 5 to about 7. Thereafter, a cellulose material is recovered therefrom which has an increased susceptibility to hydrolysis by cellulase.

Processes of the invention provide cellulose pretreatment processes which are simple and inexpensive to conduct. As well, the processes lead to pretreated cellulose materials which are much more highly susceptible to cellulase-catalyzed hydrolysis than the starting cellulose materials. Processes of the invention further employ standard equipment and do not necessarily include costly reagents or microbiological elements while nevertheless providing advantageously pretreated materials.

Additional embodiments, features and advantages of the invention will be apparent from the following description.

DESCRIPTION OF THE PREFERRED EMBODIMENTS

Figure 1:
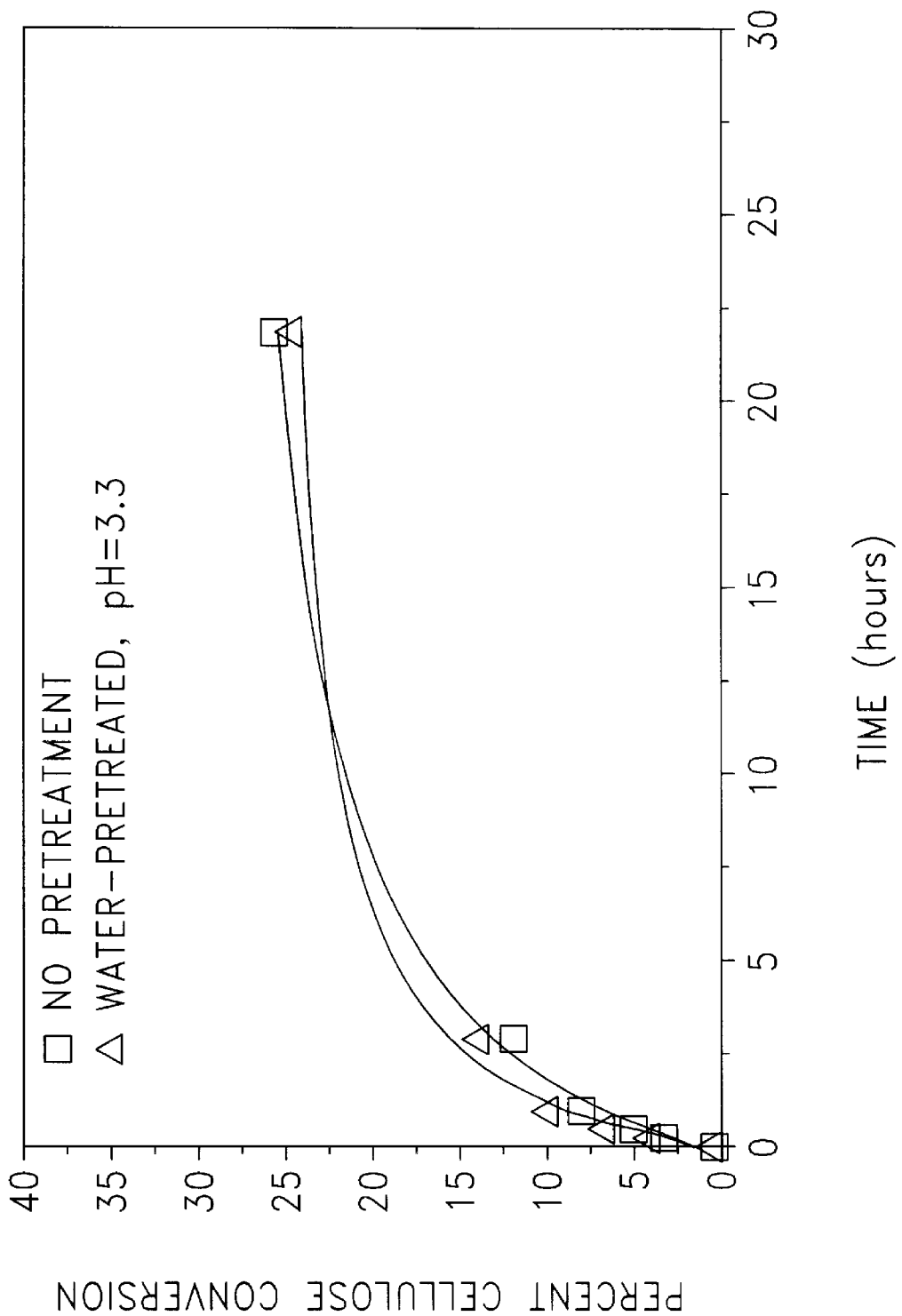
FIG. 1 is a graph illustrating the enzymatic conversion of microcrystalline cellulose after water pretreatment without pH regulation during the pretreatment.

In order to promote an understanding and appreciation of the present invention, certain preferred embodiments thereof will be described. It will be understood that only the preferred embodiments are described and that all modifications and further utilizations of the principles of these embodiments as would occur to those ordinarily skilled in the art to which the invention relates are contemplated as being a part of the invention.

As indicated above, the present invention provides processes for pretreating cellulosic materials to improve their characteristics relative to cellulase-catalyzed hydrolysis, and also to overall processes for achieving hydrolysis of cellulosic materials. In this regard, the particular cellulosic material employed in the present invention is not critical, and can be for example derived from plant biomass such as wood, agricultural products including oilseeds such as rapeseed (*Brassica napus*), and soybeans, cowpeas, corn, corn fiber, wheat, rice, barley, sugar cane bagasse, cotton, cotton, cotton-containing textiles, and the like. Cellulosic residues for use in the invention can also be obtained from municipal solid wastes, pulping wastes and pulping sludges, waste newsprint, yard wastes, etc. Other forms of cellulose materials, for example microcrystalline cellulose, are also suitable for use in the invention.

When the cellulose material is plant biomass, in one aspect of the invention it is preferred that the material contain substantial amounts of hemicellulose and lignin which occur naturally with the cellulosic material. Thus, as used herein, the term "crude plant biomass material" and variations thereof refer to plant biomass which has not been subjected to any processing steps to substantially remove hemicellulose or lignin. As discussed more fully below, it is believed that crude plant biomass materials possess a self-buffering capacity and also contain materials which act as intercalating agents in the pretreatment process. These naturally occurring properties are advantageous and can lead to pretreatments which are simple and inexpensive since in many cases no additional measures of pH control or addition of extraneous intercalating agents are necessary.

In accordance with the invention, the cellulosic material to be pretreated is generally charged with water to a reaction vessel to form a pretreatment medium. In preferred processes, the pretreatment medium will contain up to about 30% by weight of cellulosic material, most often falling in the range of about 2% to about 30% by weight. The reaction vessel will generally be equipped to operate under pressures sufficient to substantially maintain the water in a liquid state throughout the pretreatment process, i.e. to prevent any substantial formation of water vapor, and to avoid any explosive decompression of the cellulosic materials employed. Operating pressures at or above the saturation pressure of water at the temperatures of the pretreatment are thus contemplated for use in the invention. In addition, to safeguard against any flashing (i.e. formation of water vapor), it is preferable operate at pressures substantially above the saturation vapor pressure of water at the temperature employed, e.g. at least about 10 psig or more above such saturation vapor pressure.

Processes of the invention can be advantageously carried out wherein the pretreatment medium substantially fills the volume of the reaction vessel to minimize the head space available for vapor formation. However, it will be understood that this is not critical to the invention as vessels with larger head spaces can readily be employed so long as appropriate pressures are maintained to minimize vapor formation.

The pretreatment medium will generally be heated to a temperature above the glass transition temperature of the cellulosic material employed but not so high as to lead to substantial autohydrolysis of the cellulosic material. Generally speaking, temperatures of at least about 160° but not substantially exceeding about 220° C. have been suitable for these purposes. Throughout the period that the pretreatment medium is above 160° C., it is important in the present invention that its pH be maintained in the range of about 5 to about 8 so as to avoid acid or base catalyzed reactions which significantly chemically alter the cellulose. Where crude plant biomass materials are employed, as noted above it has been discovered that these materials can have a self-buffering capacity and thus in many cases no further pH control is necessary. However, where plant biomass materials or microcrystalline cellulose or other materials are employed, it is often necessary to initiate pH control in the pretreatment medium. Such pH control can be achieved using suitable basic agents, for example preferably including metal hydroxides such as alkali or alkaline earth metal hydroxides, e.g. sodium or potassium hydroxide, or other hydroxide bases such as ammonium hydroxide. In preferred processes, such basic materials are periodically added during the heating period to maintain the pH in the desired range of 5 to 8 so as to avoid autohydrolysis of the cellulose. In addition, some cellulosic materials may have an alkaline pH, initially. In such cases small amounts of acid can be used to adjust and control the pH to be between 5 and 8. Suitable acids for these purposes include inorganic or organic acids, for example sulfuric, hydrochloric, phosphoric, nitric, acetic, citric or formic acid. In using these acids, care must be taken to avoid any substantial hydrolysis of the cellulosic materials to achieve the desired pretreatment effects. The pH can be monitored for these purposes using standard equipment.

The duration of the heating period will vary in accordance with the cellulosic materials involved, the pretreatment temperatures employed, and other similar factors. In some cases it will be necessary only to slowly bring the pretreatment medium to the top pretreatment temperature desired, and then immediately allow the medium to cool (i.e. there is no hold of the pretreatment at the high temperature). In other cases, it will be desirable to maintain the pretreatment medium at the 160° C. to 220° C. temperature for some period of time to allow the desired changes to the cellulosic material. In typical processes the temperature will be held within the 160° C. to 220° C. range for up to about 5 hours, more typically up to about 3 hours.

Temperature control can be accomplished in a known manner using standard heating and monitoring equipment. As well, it is known that the temperature of thermally saturated water in a closed vessel can be controlled by venting steam to decrease the temperature. Hence a similar approach can be used in the present invention, wherein the temperature can be rapidly decreased to below that required for pretreatment by flashing of a measure amount of steam, thereby cooling the remaining water. While not particularly energy efficient, partial flashing can provide a method whereby temperature can be readily controlled as needed to quench the temperature and/or prevent temperature and pressure overshot.

Preferred processes of the invention will modify a starting cellulose material so as to at least double its susceptibility to cellulase-catalyzed conversion to glucose over a given period of time, say about 40 hours, as more particularly described in the Experimental below. More preferred inventive process can provide pretreated cellulose materials which are greater than three times and even up to about 10 times as susceptible to such conversion to glucose, as depicted for example in FIG. 3.

In carrying out processes of the invention, heat from pretreatment mediums can be recovered and used in subsequent pretreatments. For example, heat recovery by countercurrent passage of hot fluid containing preheated slurry over heat exchangers such as heat exchange tubes through which incoming slurry (to be subjected to pretreatment) is passed. In this manner, the outgoing, finished pretreatment slurry is cooled and in turn heats the incoming pretreatment slurry. Process economics can thereby be improved by recovering energy supplied to the heating process.

Additionally, in accordance with the invention the pretreatment medium can include other conventional additives such as surfactants, e.g. vegetable oils such as soybean oil, canola oil, and others, to serve as intercalating agents. As well, pretreatments of the invention can be used in combination with other pretreatment procedures, for example microbiological pretreatments, as illustrated in the Experimental below.

In order to promote a further understanding of the invention and its advantages, the following specific Experimental is provided. It will be understood that this Experimental is illustrative and not limiting in nature.

EXPERIMENTAL

Plant Growth

Rapeseed and cowpea plants were grown in the Horticulture Department at Purdue University (Frick, 1993; Ohler, 1994). Plants were grown until maturity, and then harvested. Upon harvesting, the inedible portions of the plant material were air dried for several days prior to being oven dried for 2 days between 70°–75° C. The plant materials, divided into stem, leaf, and seed pod (or hull portions), were then ground to between 20–40 mesh (0.84–0.43 mm). The ground material was stored in sealed glass containers until use.

Carbohydrate Analysis

Proximate analysis of the cellulosic materials was conducted. Fat determination was by Soxhlet extraction (AOAC method 920.39B). Protein was by the microKjeldahl method (AOAC 960.52), and ash determination was per AOAC 923.03. Moisture contents were determined by oven drying (104° C., 24 h). Since assays for protein and ash were on defatted samples, the values were normalized to reflect the protein and ash contents of the original sample. The established conversion factor of 6.25×N was used to obtain the protein content. Total carbohydrate (CHO) concentration was calculated from the moisture, protein and fat values: Total CHO=100%−(% protein+% fat+% ash+% moisture).

Further investigations into the amounts of specific carbohydrate components were also conducted. Data were obtained on a dry weight basis using both the acid detergent fiber (ADF) procedure and the neutral detergent fiber (NDF) procedure of Goering and Van Soest (1970), and Van Soest and Wine (1967). ADF is comprised of lignin, cellulose, and insoluble minerals while the NDF also includes hemicellulose. Therefore, subtracting the ADF value from the NDF value gives the weight of the hemicellulose in the sample. The amount of lignin in the samples was found using the permanganate lignin assay of Van Soest and Wine (1968).

Enzyme Activity

Cellulase enzyme systems evaluated included Cytolase CL, Rhozyme HP-150, Multifect XL, and Cytolase M103S, all from Genencor International, Schaumburg, Ill. Conditions for the measurement of cellulase activities were as reported by Ghose (1987) and included filter paper activity (FP), cellobiase activity and CMCase activity. A glucose analyzer (Glucose Analyzer II, Beckman Instruments, Fullerton, Calif.) was also used to measure the amount of glucose present following hydrolysis. Alternatively, the amount of glucose as well as other oligosaccharides was calculated from the use of liquid chromatography (LC) using appropriate standard curves. The LC system used and its operation were as described by Lin et al. (1988). The percentage hydrolysis of the plant cellulosic material was calculated by the following equation:

(g glucose produced) $\left[\dfrac{162}{180}\right]$ (100%) dry weight of the cellulose.

The cellulose hydrolysis assay developed for the plant material was as follows: to 100 mg of the plant material, one ml of the enzyme solution (diluted to between 1 to 90 filter paper units (FPU)/g substrate with 0.05M citrate buffer, pH 4.8 and prewarmed to 50° C.) was added. The contents of the tubes were mixed, covered, and incubated at 50° C. At time intervals, 30 microliter portions were removed and microfuged for 1.5 minutes. The supernatant portion was then injected into the glucose analyzer for glucose concentration determination. In some cases, samples were frozen for LC investigation. Duplicate or triplicate samples were analyzed along with appropriate enzyme and substrate blanks.

Water Pretreatment

Both microcrystalline cellulose and plant materials as described above were pretreated in a 300 mL pressure reactor (Autoclave Engineers, Erie, Pa.) as described by Kohlmann et al (1993). The microcrystalline cellulose (Avicel, FMC, Newark, Del.) was sieved dry to give a material with an initial particle size of greater than 53 microns. The reactor was loaded with 135 ml of deionized distilled water containing 1.5–5 weight % fiber particles. For the plant material, the reactor was heated to 180° or 200° C., the time required to reach these temperatures being 30–40 minutes. Microcrystalline cellulose was heated up to 220° C. over approximately 2 hours. The pretreated materials were collected through a sample port which emptied into a cooled coil, having sufficient back pressure to avoid flashing. The plant materials were treated with enzyme (at 15 mg enzyme protein/g plant material) following air drying for 3–4 days (moisture content 6–8%). Cellulase enzyme was added (at 15 mg enzyme protein/g cellulose material) directly to portions of the pretreated microcrystalline cellulose. The amount of protein solubilized by the water pretreatment was measured in the supernatant fraction using the bicinchoninic (BCA) protein assay (Smith et al., 1985). Scanning Election Microscopy (SEM) was conducted on a Jeol (JSM-T300) microscope.

Microbiological Methods

P. ostreatus (NRRL 2366) was obtained in the form of mycelial growth on a potato dextrose agar (PDA) slant from the Northern Regional Research Laboratory (NRRL) in Peoria, Ill. Initial transfers were made by adding deionized distilled water (DDW), 1–2 ml to the original slant and then using this liquid to prepare streak plates on PDA agar. The plates were incubated several days at room temperature before new PDA slants were prepared from individual colonies. The new slants were incubated for two days at room temperature before being used to inoculate liquid nutrient media to produce submerged cultures.

Modified procedures of Kaneshiro (1977), and Lindenfelser et al. (1979), were used to inoculate either rapeseed or cowpea stems with the submerged P. ostreatus pellets. Flasks containing wetted stems (100 g H₂O/20 g stems) were sterilized and allowed to cool. Using aseptic conditions, 10 ml of the submerged culture media was added to each flask containing stems. Appropriate controls were also prepared. Incubation was for 30 days at 27° C.; growth was visible after two days. During incubation, sterile DDW was added periodically to moisten the plant stems.

RESULTS

Compositional Analysis

Proximate analysis data for rapeseed, cowpea and rice samples is presented in Table 1. Individual carbohydrate components by ADF and NDF procedures are given in Table 2.

The carbohydrate values calculated by difference (Table 1) with some exceptions agree with values obtained through fiber analysis (Table 2), and indicate the large amount of inedible material in the stems, seed pods and leaves. The values reported in Table 2 should be more accurate for determination of total CHO content in these materials.

TABLE 1

Proximate Analysis of Inedible Plant Material[1].

| Plant/Portion | Carbohydrate | Protein | Fat | Ash | Total |
|---|---|---|---|---|---|
| Rapeseed | | | | | |
| Stems | 73 | 15 | 1 | 11 | 100 |
| Siliques | 68 | 22 | 1 | 10 | 101 |
| Leaves | 50 | 45 | 2 | 11 | 108 |
| Cowpea | | | | | |
| Stems | 87 | 4 | 1 | 8 | 100 |
| Leaves | 46 | 34 | 4 | 16 | 100 |
| Pods | 66 | 27 | 2 | 5 | 100 |
| Rice | | | | | |
| Leaves | 51 | 35 | 2 | 12 | 100 |
| Stems | 61 | 21 | 1 | 17 | 100 |

[1]Percentage dry weight basis.

TABLE 2

Carbohydrate/Lignin Composition of Inedible Plant Material[1].

| Plant/Portion | Cellulose | Hemicellulose | Lignin | Total |
|---|---|---|---|---|
| Rapeseed | | | | |
| Stems | 38 | 10 | 18 | 66 |
| Siliques | 35 | 12 | 18 | 65 |
| Leaves | 14 | 15 | 5 | 34 |
| Cowpea | | | | |
| Stems | 27 | 16 | 9 | 52 |
| Pods | 37 | 17 | 15 | 69 |
| Leaves | 11 | 12 | 5 | 28 |
| Rice | | | | |
| Stems | 33 | 31 | 12 | 76 |
| Hulls | 34 | 19 | 10 | 63 |
| Leaves | 27 | 27 | 4 | 58 |

[1]Percentage dry weight basis ±5%.

Enzymatic Hydrolysis

Several commercially available enzyme preparations were screened for the ability to hydrolyze cellulose present in the stem, leaf or seed pod fractions of rapeseed, cowpea and rice plants (Table 3). Cytolase CL was chosen for evaluation of effectiveness of pretreatments because overall glucose production was higher with this enzyme system.

TABLE 3

Percentage Cellulose Hydrolysis to Glucose Following a 24 hour Incubation with Enzymes.

| Plant Material | Cytolase CL | Multifect XL | Cytolase M103S | Rhozyme HP-150 |
|---|---|---|---|---|
| Rapeseed | | | | |
| Stems | 23 | 15 | 22 | 9 |
| Siliques | 11 | 11 | 17 | 5 |
| Rice | | | | |
| Leaves | 23 | 37 | 8 | 2 |
| Stems | 8 | 13 | 7 | 0 |
| Hulls | 23 | 29 | 6 | 15 |
| Cowpea | | | | |
| Stems | 61 | 57 | 34 | 21 |
| Pods | 36 | 34 | 34 | 7 |
| Leaves | 49 | 20 | — | 3 |

Water Pretreatment of Microcrystalline Cellulose

Enzymatic hydrolysis of crystalline cellulose (Avicel) following water pretreatment at 220° C. is shown in FIG. 1. As depicted in FIG. 1, there is only a small enhancement in the initial rate of Avicel hydrolysis, but by 24 h the rate and extent of hydrolysis were equivalent to control samples. Other characteristics of the pretreated Avicel were a decrease in pH from 5.4 to 3.3 and considerable browning (degradation) of the Avicel. Avicel was also pretreated at 220° C., while maintaining the pH between 5.5 and 7.0 during the heating period by the periodic addition of KOH, as described by Kohlmann et al., 1993. The results are presented in FIG. 2.

Water Pretreatment of Plant Material

Figure 3:
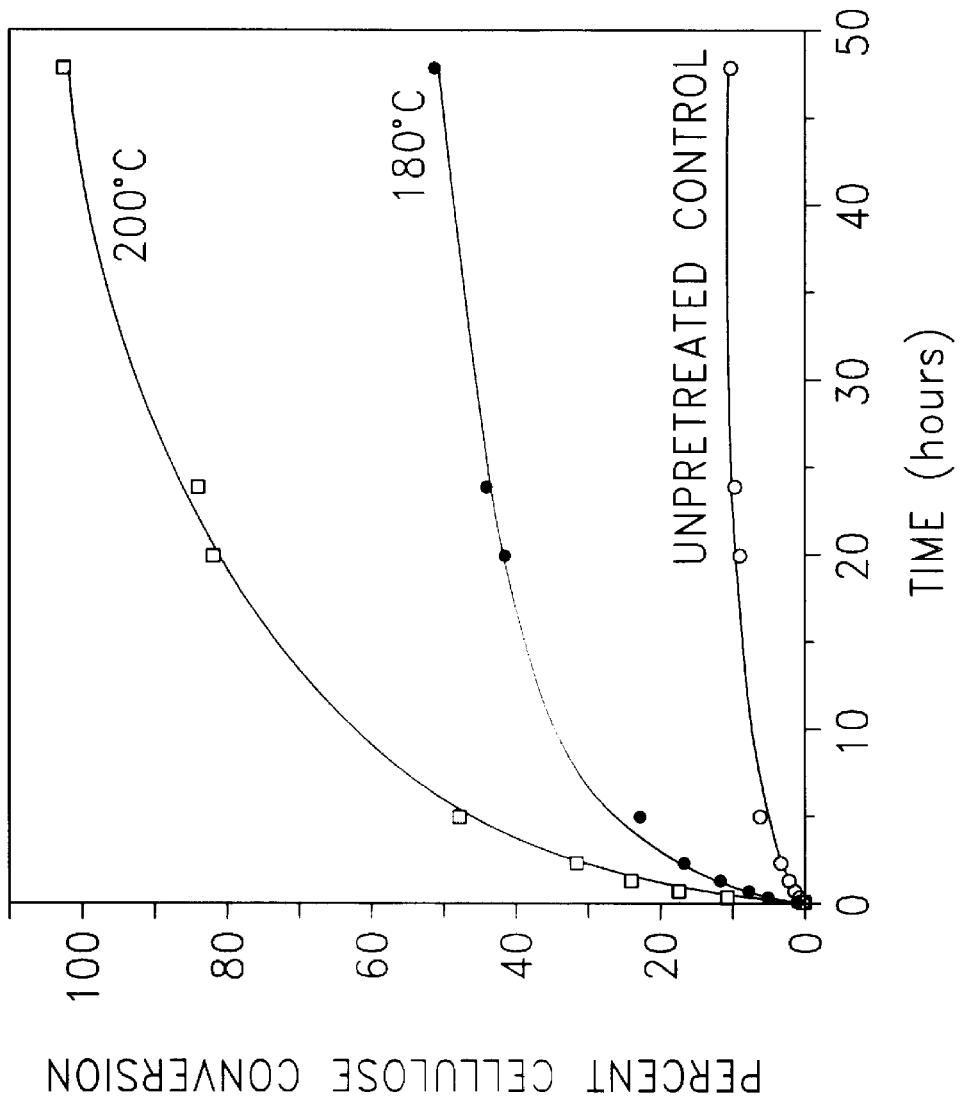
FIG. 3 is a graph illustrating the enzymatic conversion of water pretreated rapeseed stems.
Figure 4A:
FIGS. 4(A)–(C) provide photomicrographs of control and water pretreated rapeseed stems: (A) Control, (200×); (B) 180° C., (200×); (C) 200° C., (350×).
Figure 4B:
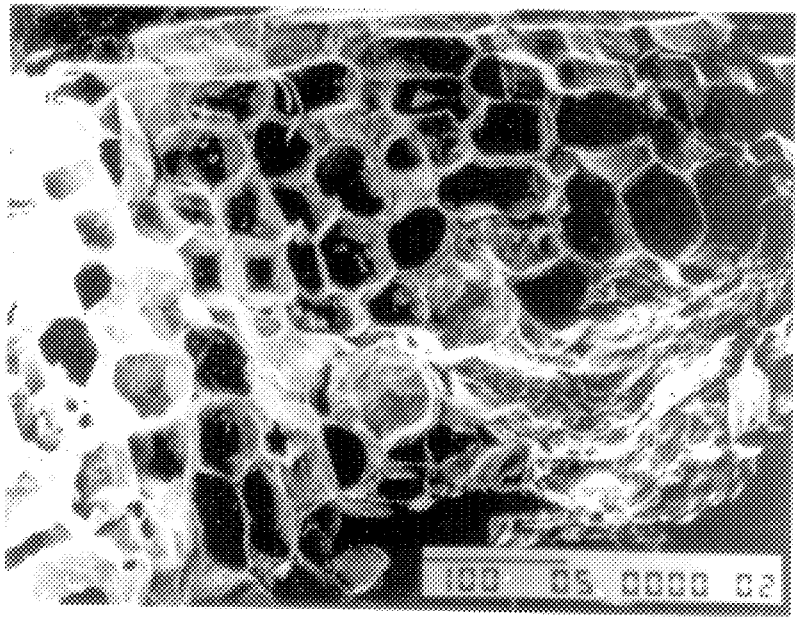
Figure 4C:
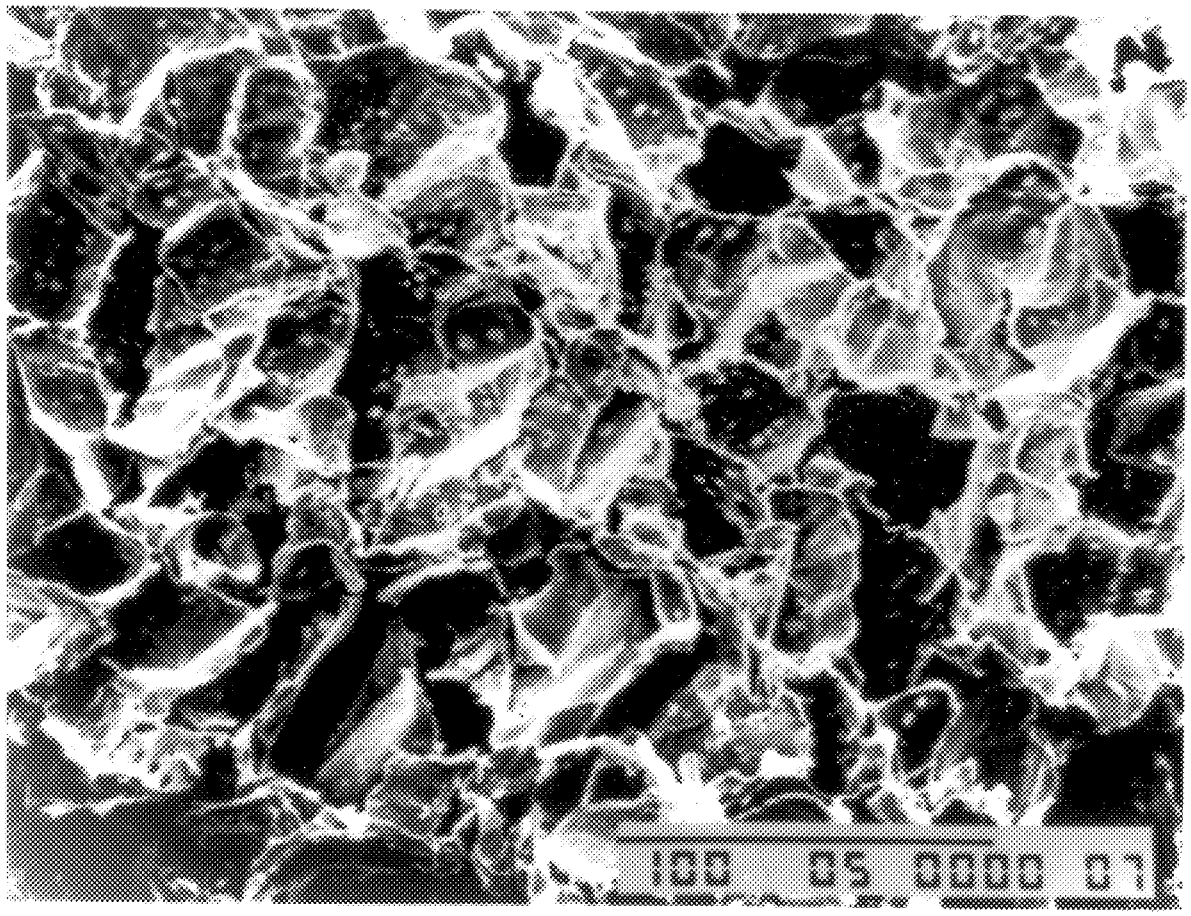

Hot water treatment of plant stems at 180° C. and 200° C. resulted in significant improvement of the enzymatic hydrolysis of the cellulose in the material (FIG. 3). Both the rate and the extent of cellulose conversion to glucose were enhanced. Compositional, chemical and physical changes, all possibly related to this enhanced susceptibility to enzymatic action, were noticed in the plant material following the water pretreatment. Scanning electron microscopy (SEM) on control and heated rapeseed stems produced the photomicrographs presented in FIGS. 4(A)–(C), in which (A) is the control, (B) is material heated to 180° C., and (C) is material heated to 200° C.

Compositional changes in carbohydrate components following the water pretreatment are given in Table 4. Water pretreatment of rapeseed reduces the fraction of hemicellulose which remains, and is accompanied by an apparent increase in cellulose content. The fraction of lignin appears to be constant, thus indicating that in relative amounts, water removes some lignin. Approximately half the protein in the stem samples was solubilized as detected by the BCA protein assay in the supernatant portion of the heat treated material.

Unlike the crystalline Avicel (FIG. 2), the pH of the plant material did not decrease dramatically, and hence represented a self-buffering material. In most cases the pH dropped about one pH unit (Table 5).

Biological Pretreatment

Figure 5:
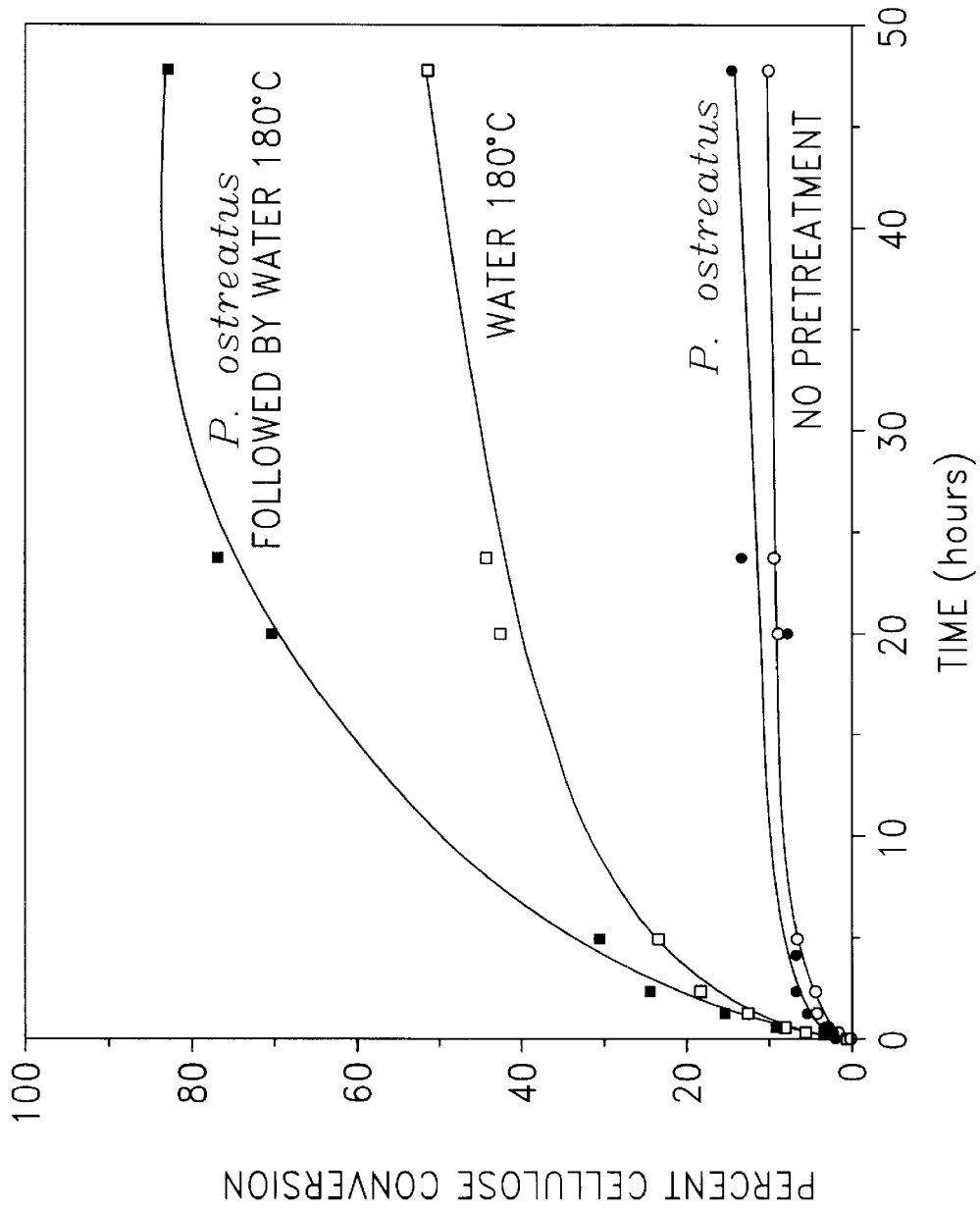
FIG. 5 shows the enzymatic conversion of pretreated rapeseed stems.
Figure 6:
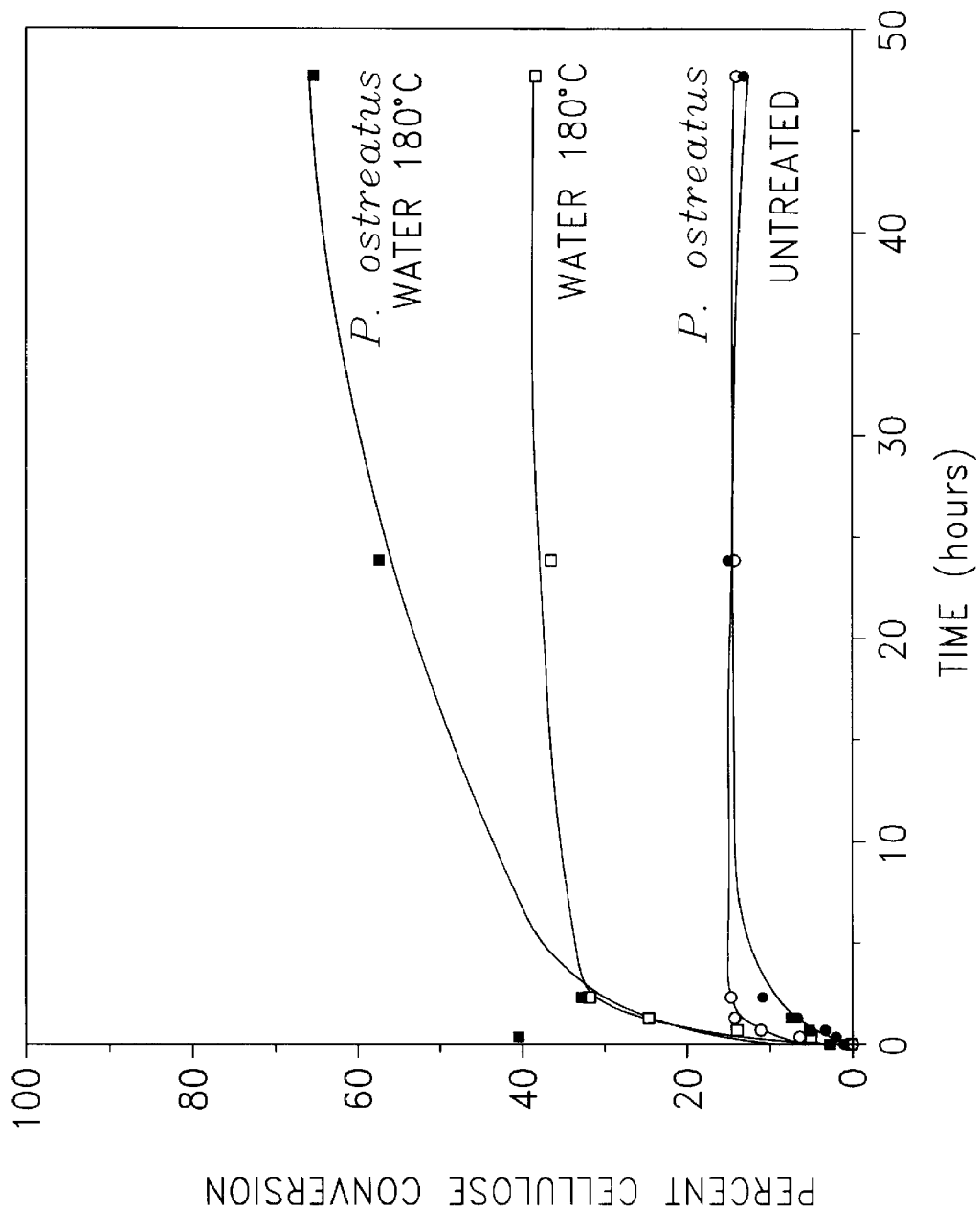
FIG. 6 shows the enzymatic conversion of pretreated cowpea stems.

Mycelial growth of *P. ostreatus* alone as a pretreatment did not increase the susceptibility of the cellulose to enzyme action, but when the growth was followed by the hot water treatment, a significant increase in glucose production was measured (FIGS. 5 and 6). Other associated changes following growth and heating to 180° C. were a reduction in the hemicellulose content (Table 4). Liquid chromatography of the supernatant fraction indicated that little breakdown of hemicellulose to mono and disaccharide components was occurring (data not shown). The amount of xylose and arabinose present in the supernatant fraction following heating would correspond to a less than 1% degradation of hemicellulose. It is likely that the hemicellulose is present in soluble larger molecular weight fractions.

TABLE 4

Carbohydrate Composition of Rapeseed Stems Following Water Pretreatment.

| | Percentages (dry weight basis ±5%) | | |
|---|---|---|---|
| Treatment | Hemicellulose | Cellulose | Lignin |
| Control | 17 | 32 | 28 |
| 180° C. | 4 | 50 | 24 |
| 200° C. | 0 | 66 | 28 |

TABLE 5

Effect of Pretreatment on pH.

| Material | Initial pH | Final pH |
|---|---|---|
| Rapeseed Stems | | |
| 180° C. | 5.7 | 4.7 |
| 200° C. | 5.7 | 4.3 |
| Soybean Hulls | 6.6 | 4.8 |
| Rice Stems and Leaves | 5.8 | 5.6 |

DISCUSSION

Water Pretreatment of Microcrystalline Cellulose

In an effort to understand pretreatment effects on cellulose, a model was developed to predict cellulose and glucose degradation during aqueous heating (Weil, 1993). At a pH below 7.0, the degradation reactions are catalyzed by H+. Two of the primary degradation products, formic and levulinic acid, contribute significant quantities of hydrogen ions. Hence, as degradation progresses, the rate of degradation increases.

Figure 2:
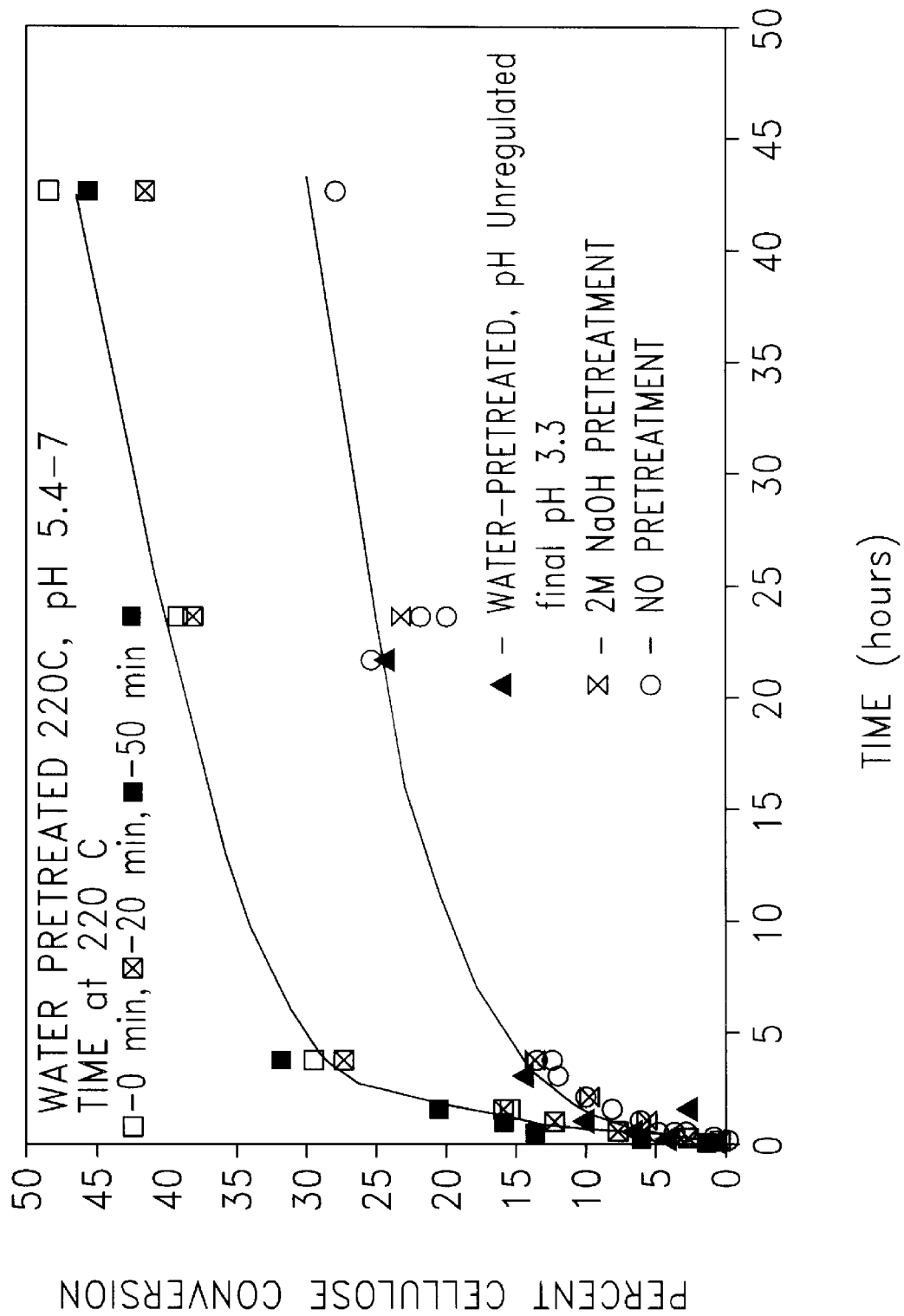
FIG. 2 is a graph illustrating the enzymatic conversion of microcrystalline cellulose after water pretreatment while controlling pH in accordance with the invention.

The applicants have controlled pH during pretreatment by continuously adding small amounts of 0.5M KOH solution when the Avicel is at high temperatures. By adding ~12 mL of KOH solution, the pH was maintained between 5.5 and 7 for the entire heat up profile and for a substantial time at 220° C. (FIG. 2). This resulted in a significant decrease in degradation and enhanced enzymatic hydrolysis as shown in FIG. 2. This clearly shows that liquid water pretreatment at high temperatures can enhance the susceptibility of crystalline cellulose to hydrolysis. Further enhancements were not seen by increasing the time at 220° C. or the pretreatment temperature (FIG. 2). This is most likely due to the small amount of degradation that occurred during these conditions. Improved pH control may result in even greater susceptibility of Avicel.

Water Pretreatment of Plant Material

Enhanced Enzymatic Reactivity. The use of liquid water at 180° C. to treat inedible plant material improved the subsequent enzymatic hydrolysis of the treated material (FIG. 3), to 60% to 90%. Complete conversion of the cellulose by enzymatic hydrolysis was observed for materials pretreated by bringing the material to 200° C., and then immediately allowing it to cool. Compared to crystalline cellulose, plant materials are complex and experience compositional, chemical and physical changes following water pretreatment, some of which may relate to the enhanced enzymatic reactivity.

Changes in Carbohydrate Composition. The primary compositional change which occurred as a result of the pretreatment was solubilization of most of the hemicellulose present (Table 4). The hydrolysis of the hemicellulose was assumed to be minimal since LC showed lack of xylose and furfural compounds. Hemicellulose is physically associated with cellulose, and hemicellulose removal is known to increase pore volume, thereby increasing enzyme accessibility and hydrolysis (Grethlein, 1985; Marsden and Gray, 1986). Mok and Antal (1992), noted that hemicellulose can easily be removed from biomass by treatment with dilute acid, but they also found that this same goal can occur with water alone, achieving complete hemicellulose removal using water between 200°–230° C.

The amount of lignin present in the rapeseed stems does not appear to change following heat treatment in water (Table 4). It has been reported that little delignification occurs until temperatures exceed 180° C. (Faass et al, 1989). However, chemical bonds between cellulose and lignin may have been affected. Meshitsuka 1991, states that at temperatures higher than the softening temperature of lignin (60°–80° C.), and close to that of cellulose (230°–253° C.), the melted lignin separates and then coagulates into cellulose free particulates. Lignin is also converted to a form which is extractable in alkali and some organic solvents. The temperatures used to pretreat the cellulose are well above the softening temperature of lignin, but non-alkaline; therefore, the lignin may have been rearranged or separated from the cellulose, but not solubilized and removed. This rearrangement of the hydrophobic lignin could possibly improve enzyme access to the internal pores of the cellulose.

Following the pretreatment, the material became enriched in cellulose due to removal of hemicellulose and protein (Table 4). This is in fact desirable, providing a less heterogeneous cellulosic substrate than the original material. Meshitsuka 1991, states that under proper conditions, only a small extent of cellulose hydrolysis occurs during the steam explosion process. Conditions in the present work were less severe than those of steam explosion; therefore, cellulose hydrolysis would not be expected.

pH Effect. Plant materials were able to some extent buffer changes in pH (Table 5), possibly due to their heterogeneous structure which includes proteins, hemicellulose, and salts. Although the present invention is not limited by any theory, it is believed that pressure cooking of cellulose in liquid water at controlled pH avoids acid formation and hydrolysis of the cellulose during the pretreatment. Thus, an advantage then of pretreating plant materials in water is their ability to buffer changes in pH.

Physical Changes. The SEM photomicrographs (FIG. 4) indicate that changes are occurring on the surface of the stem material as a result of the heat treatment. Following heating at 180° C., the stems appear to contain more void than controls. At the pretreatment temperature of 200° C., the photomicrographs show a similar pattern as the 180° C. samples, but it appears that the surface is even more disrupted at the higher temperature.

The recrystallization of cellulose upon removal of the pretreatment conditions is a known phenomenon. Recrystallization reduces the reactivity of the cellulose, and therefore decreases the glucose yield achieved upon subsequent enzyme hydrolysis. The applicants have discovered that pretreated cellulose in biomass materials retains its reactivity with respect to subsequent enzyme hydrolysis, even when the cellulose is air dried to about 8% moisture. It is believed that the complex composition of biomass (which includes hemicelluloses, other oligosaccharides, and lignin) fosters retention of the reactive state of pretreated cellulose, even when the material is air dried following pretreatment to about 8% moisture. It is believed that this effect could be due to water soluble polysaccharides (hemicelluloses) whose hydrolysis is inhibited at these pretreatment conditions and which are able to insert themselves between hydrated cellulose chains and thereby act as intercalating agents during pretreatment. This would prevent the adjacent cellulose chains from recrystallizing during drying when the water is removed. Hemicelluloses would normally be hydrolyzed at conditions of water pretreatment (through autohydrolysis). However, pH control in the applicants' pretreatment process may reduce this hydrolysis, and hence maintain the water soluble oligosaccharides intact. These then could act as in situ intercalating agents during the pretreatment step. Addition of a separate intercalating agent, which would add cost to the pretreatment, can therefore be avoided.

Biological Pretreatment of Plant Material

Mycelial growth of *P. ostreatus* on plant stems did not result in enhanced glucose production following cellulase addition (FIGS. 5 and 6). However, when fungal growth on rapeseed and cowpea stems was combined with water pretreatment, cellulose conversion was greatly enhanced (FIGS. 5 and 6). Thus, the applicants have demonstrated that water pretreatment processes of the present invention can be combined with other known pretreatment methods to improve susceptibility of cellulosic materials to enzymecatatlyzed hydrolysis.

REFERENCES

The following references are hereby incorporated by reference in their entirety as if each had been individually incorporated by reference and fully set forth.

Beltrame, P. L. Carniti, P., Visciglio, A., Focher, B., and Marzett, A., 1992, Fractionation and bioconversion of steam exploded wheat straw, *Biores. Technol.* 39:165.

Bobleter, O., Niesner, R., and Rohr, M., 1976. The hydrothermal degradation of cellulosic matter to sugars and their fermentative conversion to protein, J. Appl. Polymer Sci., 20:2083.

Brownell, H. H. and Saddler, J. N., 1987, Steam pretreatment of lignocellulosic material for enhanced enzymatic hydrolysis, Biotech and Bioeng., 29:228.

Faass, G. S., Roberts, R. S., and Muzz, J. D., 1989, Buffered solvent pulping, *Holzforschung* 43(4):245.

Frick, J., 1993, "Evaluation of dwarf rapeseed (*Brassica napus*) as an oilseed crop for bioregenerative life support systems," M. S. Thesis, Purdue University, West Lafayette, Ind.

Ghose, T. K., 1987, Measurement of cellulase activities. *Pure and Appl. Chem.*, 59 (2):257.

Goering, H. K. and Van Soest, P. J., 1970, Forage Fiber Analysis, in: "*Agricultural Handbook No.* 379", Agricultural Research Service, U.S. Department of Agriculture, Washington, D.C., Jacket No. 387-598.

Grethlein, H. E., 1985, The effect of pore size distribution on the rate of enzymatic hydrolysis of cellulosic substrates, *Bio. Technol.* 3:155.

Haw, J. F., Maciel, G. E., Linden, J. C., and Murphy, V. G., 1985, Nuclear magnetic resonance study of autohydrolysis and organosolv-treated lodgepole pinewood using carbon-13 with cross polarization and magnetic-angle spinning, *Holzforschung,* 39:99.

Heitz, M., Capek-Menard, E., Koeberle, P. G., Gagne, J., Chornet, E., Overend, R. P., Taylor, J. D., and Yu, E., 1991, Fractionation of *Populus tremuloides* at the pilot plant scale: Optimization of steam pretreatment conditions using Stake II technology, *Biores. Technol.* 35:23.

Hormeyer, H. F., Schwald, W. Bonn, G., and Bobleter, O., 1988, Hydromethermolysis of birch wood as pretreatment for enzymatic saccharification, *Holzforschung,* 42(2):95.

Hudson, H. J., 1986, Fungi as decomposers of wood, in: "Fungal Biology," A. J. Willis and M. A. Sleigh, eds., Edward Arnold Ltd., London.

Kaneshiro, T., 1977, Lignocellulosic agricultural wastes degraded by *Pleurotus ostreatus, Dev. Ind. Microbiol.,* 18:591.

Kirk, T. K., and Farrell, R. L., 1987, Enzymatic combustion: The microbial degradation of lignin, Ann. Rev. Microbiol., 41:465.

Kohlmann, K., Westgate, P. J., Weil, J., and Ladisch, M. R., 1993, "Biological-based systems for waste processing." Proceedings of 1993 ICES Meeting, SAE Technical Paper Series 932251.

Ladisch, M. R., 1989. Hydrolysis, in: "Biomass Handbook," O. Kitani and C. W. Hall, eds., Gordon and Breach, New York.

Ladisch, M. R., Lin, K. W., Voloch, M., and Tsao, G. T., 1983, Process considerations in the enzymatic hydrolysis of biomass, *Enz. Microb. Technol.,* 5(2):82.

Ladisch, M. R., Ladisch, C. M., and Tsao, G. T., 1978, Cellulose to sugars: New path gives quantitative yield, *Science,* 201:743.

Ladisch, M. R., Waugh, L., Westgate, P., Kohlmann, K., Hendrickson, R., Yang, Y., and Ladisch, C., 1992, Intercalation in the pretreatment of cellulose in: "Harnessing Biotechnology for the 21st Century," M. R. Ladisch and A. Bose, eds., Proceedings of the Ninth International Biotechnology Symposium and Exposition, American Chemical Society, Washington, D.C.

Leisola, M. S. A. and Fiechter, A., 1985, New trends in lignin biodegradation, in: "Advances in Biotechnological Processes 5," Alan Liss Inc.

Lin, K. W., Jacobson, B. J., Pereira, A. N., and Ladisch, M. R., 1988, "Liquid chromatography of carbohydrate monomers and oligomers," in: "Methods in Enzymology", 160:145.

Lindenfelser, L. A., Detroy, R. W., Ramstack, J. M., and Worden, K. A., 1979, Biological modification of the lignin and cellulose components of wheat straw by *Pleurotus ostreatus, Dev. Ind. Microbiol.,* 20:541.

Marsden, W. L. and Gray, P. P., 1986, Enzymatic hydrolysis of cellulose in lignocellulosic materials, in: "CRC Critical Reviews," 3(3):235.

Meshitsuka, G., 1991, Utilization of wood and cellulose for chemicals and energy, in: "Wood and Cellulosic Chemistry," D. N. S. Hon and N. Shiraishi, eds. Marcel Dekker, Inc., New York.

Mok, W. S-L. and Antal, M. J. Jr., 1992, "Uncatalyzed solvolysis of whole biomass hemicellulose by hot compressed liquid water," *Ind. Eng. Chem. Res.,* 31: 1157.

Nidetzky, B. and Steiner, W., 1993, A new approach for modeling cellulase-cellulose adsorption and the kinetics of the enzymatic hydrolysis of microcrystalline cellulose, *Biotech. and Bioeng.,* 42:469.

Ohler, T., 1994, "Evaluation of cowpea (*Vigna unguiculata*) (L. WaLp) as a candidate species for inclusion in a CELSS," M. S. Thesis, Purdue University, West Lafayette, Ind.

Smith, P. K., Krohn, R. I., Hermanson, G. T., Mallia, A. K., Gartner, F. H., Provenzano, M. D., Fujimoto, E. K., Goeke, N. M., Olson, B. J., and Klenk, D. C., 1985, Measurement of protein using bicinchoninic acid, Analytical Biochem, 150:76.

Sjostrom, E., 1981, "Wood Chemistry Fundamentals and Applications," Academic Press, New York.

Van Soest, P. J. and Wine, R. H., 1967, Use of detergents in the analysis of fibrous foods. IV. Determination of plant cell-wall constituents, *J. Assoc. Off. Anal. Chem.,* 50:50.

Van Soest, P. J. and Wine, Determination of lignin and cellulose in acid-detergent fiber with permanganate, *J. Assoc. OffAnal. Chem.,* 54:780.

Walch, E., Zemann, A., Schinner, F., Bonn, G., and Bobleter, O., 1992, Enzymatic saccharification of helicellulose obtained from hydrothermally pretreated sugarcane bagasse and beech bark, *Biores. Technol.,* 39:173.

Weil, J., 1993, "Unified model for the hydrolytic effects during cellulose pretreatments," M. S. Thesis, Purdue University, West Lafayette, Ind.

What is claimed is:

1. A process for treatment of a cellulose-containing material, comprising:

pretreating the cellulose-containing material to increase the susceptibility of the material to enzymatic hydrolysis by a cellulase enzyme, said pretreating including combining the material and liquid water in a reactor to form an aqueous pretreatment medium, and heating the aqueous pretreatment medium to a temperature of about 160° C. to about 220° C. while maintaining the pH of the treatment medium in the range of about 5 to about 8 by the addition of base; and thereafter contacting the pretreated cellulosic material with a cellulase enzyme to enzymatically hydrolyze the cellulosic material.

2. The process of claim 1 wherein the cellulosic material is microcrystalline cellulose, and said process further comprises periodically adding base to the pretreatment medium to control its pH.

3. The process of claim 1 wherein the cellulosic material is or is derived from wood, oilseeds, cowpeas, corn, corn fiber, wheat, rice, barley, sugar cane, or cotton.

4. The process of claim 3 wherein the cellulosic material contains stems, siliques or leaves of Rapeseed plants.

5. The process of claim 3 wherein the cellulosic material contains Cowpea stems, leaves or pods.

6. The process of claim 3 wherein the cellulosic material contains Rice leaves or stems.

7. A process for enzymatically hydrolyzing a cellulosic material, comprising:

enzymatically hydrolyzing a pretreated cellulosic material in the presence of a cellulase enzyme;

said cellulosic material being the product of a pretreatment process in which the cellulosic material is heated in a liquid water medium to a temperature of about 160° C. to about 220° C. while maintaining the pH of the liquid water medium in the range of about 5 to about 8, so as to increase the susceptibility of the cellulosic material to hydrolysis by the cellulase enzyme.

8. The process of claim 7 wherein the cellulosic material is microcrystalline cellulose, and said pretreatment process further comprises periodically adding base to the pretreatment medium to control its pH.

9. The process of claim 7 wherein the cellulosic material is or contains components of wood, oilseeds, cowpeas, corn, corn fiber, wheat, rice, barley, sugar cane, or cotton.

10. The process of claim 7 wherein the cellulosic material contains stems, siliques or leaves of Rapeseed plants.

11. The process of claim 7 wherein the cellulosic material contains Cowpea stems, leaves or pods.

12. The process of claim 7 wherein the cellulosic material contains Rice leaves or stems.

13. A process for pretreating microcrystalline cellulose to increase its susceptibility to hydrolysis by a cellulase enzyme, and for hydrolyzing the pretreated microcrystalline cellulose, comprising:

pretreating microcrystalline cellulose by heating the microcrystalline cellulose in a liquid water medium at a temperature of about 160° C. to about 220° C.;

controlling the pH of the liquid water medium during the period that it is in said temperature range, so as to maintain the pH of the liquid water medium in the range of about 5 to about 8; and recovering therefrom a pretreated microcrystalline cellulose having an increased susceptibility to hydrolysis by a cellulase enzyme; and enzymatically hydrolyzing the pretreated microcrystalline cellulose in the presence of a cellulase enzyme.

14. The process of claim 13 wherein said controlling the pH includes adding base to the liquid water medium.

15. The process of claim 14 wherein the base is an alkali metal hydroxide, an alkaline earth metal hydroxide, or ammonium hydroxide.

16. The process of claim 15 wherein the base is sodium or potassium hydroxide.

17. The process of claim 15 wherein the base is ammonium hydroxide.

18. The process of claim 16 wherein the base is potassium hydroxide.

19. A process for hydrolyzing a crude plant cellulose material containing hemicellulose and lignin and which has been pretreated to increase the susceptibility of the cellulose material to hydrolysis by a cellulase enzyme, comprising:

hydrolyzing a pretreated cellulose material in the presence of a cellulase enzyme, wherein said pretreated cellulose material is the product of a process which comprises:

charging water and a crude plant cellulose material containing lignin and hemicellulose to a reactor to form a pretreatment mixture; and heating the pretreatment mixture to a temperature of at least about 160° C. but not exceeding about 220° C., the pH of the pretreatment mixture during said heating being in the range of about 5 to about 8;

thereby forming said pretreated cellulose material having an increased susceptibility to hydrolysis by said cellulase enzyme.

20. The process of claim 19 wherein the cellulosic material contains stems, siliques or leaves of Rapeseed plants.

21. The process of claim 19 wherein the cellulosic material contains Cowpea stems, leaves or pods.

22. The process of claim 19 wherein the cellulosic material contains Rice leaves or stems.

23. A process for hydrolyzing a pretreated cellulosic material, comprising:

enzymatically hydrolyzing a pretreated cellulosic material in the presence of a cellulase enzyme, said pretreated cellulosic material being the product of a process which comprises:

providing a pretreatment medium containing a cellulosic material in water;

heating the pretreatment medium in a reaction vessel at a pressure at or above the saturation vapor pressure of water at the temperature of the heating, and while maintaining the pH of the medium at a value at which no substantial acid- or base-catalyzed autohydrolysis of the cellulosic material occurs; and causing the pretreatment medium to cool and the pressure to dissipate so as to avoid explosive decompression of the cellulosic material;

so as to increase the susceptibility of the cellulosic material to cellulase-catalyzed hydrolysis.

* * * * *

UNITED STATES PATENT AND TRADEMARK OFFICE
CERTIFICATE OF CORRECTION

PATENT NO. : 5,846,787
DATED : December 8, 1998
INVENTOR(S) : Michael R. Ladisch et al.

It is certified that error appears in the above-indentified patent and that said Letters Patent is hereby corrected as shown below:

In col. 14, line 11, please insert --R.H., 1968,-- after "Wine,".

In col. 14, line 15, please delete "helicellulose" and insert in lieu thereof --hemicellulose--.

Signed and Sealed this

Tenth Day of August, 1999

Q. TODD DICKINSON

*Attest:*

*Attesting Officer*    *Acting Commissioner of Patents and Trademarks*